US011896600B2

(12) United States Patent
Prasad

(10) Patent No.: US 11,896,600 B2
(45) Date of Patent: Feb. 13, 2024

(54) COMPOSITION AND METHOD OF USING EICOSANOYL-5-HYDROXYTRYPTAMIDE FOR TREATING NEURODEGENERATIVE DISORDERS

(71) Applicant: Kodimule Shyam Prasad, Bangalore (IN)

(72) Inventor: Kodimule Shyam Prasad, Bangalore (IN)

(73) Assignee: Vidya Herbs, Inc., Fullerton, CA (US)

( * ) Notice: Subject to any disclaimer, the term of this patent is extended or adjusted under 35 U.S.C. 154(b) by 524 days.

(21) Appl. No.: 17/026,263

(22) Filed: Sep. 20, 2020

(65) Prior Publication Data

US 2021/0085690 A1   Mar. 25, 2021

Related U.S. Application Data

(60) Provisional application No. 62/903,800, filed on Sep. 21, 2019.

(51) Int. Cl.
| | |
|---|---|
| *A61K 31/559* | (2006.01) |
| *A61K 31/4045* | (2006.01) |
| *A61K 36/74* | (2006.01) |
| *A61P 25/28* | (2006.01) |
| *A61K 9/00* | (2006.01) |
| *A61K 31/522* | (2006.01) |
| *A61K 31/216* | (2006.01) |

(52) U.S. Cl.
CPC ........ *A61K 31/559* (2013.01); *A61K 31/4045* (2013.01); *A61K 36/74* (2013.01); *A61P 25/28* (2018.01); *A61K 9/0053* (2013.01); *A61K 31/216* (2013.01); *A61K 31/522* (2013.01)

(58) Field of Classification Search
CPC .............. A61K 31/4045; A61K 31/522; A61K 31/559; A61K 36/74; A61K 31/216; A61K 9/0053; A61P 25/28; C12Q 1/6886; C12Q 2600/158; C12Q 2600/178
See application file for complete search history.

(56) References Cited

U.S. PATENT DOCUMENTS

| | | | |
|---|---|---|---|
| 4,628,052 A | 12/1986 | Peat | |
| 8,377,429 B2 | 2/2013 | Scannon | |
| 9,775,822 B2 | 10/2017 | Prasad | |
| 9,962,356 B2 | 5/2018 | Prasad | |
| 10,039,303 B2 | 8/2018 | Takeuchi | |
| 10,420,744 B2 | 9/2019 | Prasad | |
| 10,588,885 B2 | 5/2020 | Prasad | |
| 10,952,985 B2 | 3/2021 | Prasad | |
| 11,000,497 B2 | 5/2021 | Prasad | |
| 11,607,398 B2 | 3/2023 | Prasad | |
| 2004/0110938 A1 | 6/2004 | Parekh | |
| 2011/0223281 A1 | 9/2011 | Ibarra | |
| 2011/0313014 A1 | 12/2011 | Robert | |
| 2014/0314727 A1 | 10/2014 | Singh | |
| 2015/0209399 A1 | 7/2015 | Fields | |
| 2015/0335673 A1 | 11/2015 | Yamada | |
| 2016/0081967 A1 | 3/2016 | Prasad | |
| 2017/0231955 A1* | 8/2017 | Stock ..................... A61K 36/74 |
| | | | 514/415 |
| 2018/0028482 A1 | 2/2018 | Prasad | |
| 2018/0311198 A1 | 11/2018 | Prasad | |
| 2019/0111015 A1 | 4/2019 | Prasad | |
| 2020/0138765 A1 | 5/2020 | Prasad | |
| 2021/0283088 A1 | 9/2021 | Prasad | |

FOREIGN PATENT DOCUMENTS

| | | |
|---|---|---|
| JP | 2008189681 A1 | 8/2008 |
| WO | 2014138426 | 9/2014 |
| WO | 2015050023 A1 | 4/2015 |
| WO | 2014104157 A1 | 11/2015 |

OTHER PUBLICATIONS

Farah (in Coffee: Emerging Health Effects and Disease Prevention, First Edition. Edited by Yi-Fang Chu., 2012 John Wiley & Sons, Inc. Published 2012 by Blackwell Publishing Ltd).
Murase et al. Am J Physiol Endocrinol Metab 300: E122-E133, 2011.
Venkatesh et al., J. Pharm. Sci. 89, 145-54 (2000).
Monteiro The Journal of Nutrition, Journal of Nutrition (2007), 137(10), 2196-2201.
Meng et al.; Roles of Chlorogenic Acid on Regulating Glucose and Lipids Metabolism: A Review, Evidence-Based Complementary and Alternative Medicine, vol. 2013, Article ID 801457, pp. 1-11 (2013).
Weisz et al. ("Identification and quantification of phenolic compounds from sunflower (*Helianthus annuus* L.) kernels and shells by HPLC-DAD/ESI-MSn," Food chemistry, vol. 115, No. 2, pp. 758-765 (2009)).
Gray "Caffeoylquinic acids in Centella asiatica protect agains beta-amyloid toxicity" J alz dis 40(2):359-373 (2014).
Kwon "Neuroprotective effects of chlorogenic acid on scopolomine-induced amnesia via anti-acetylcholinesterase and anti-oxidative activities in mice" Euro J pharma 649:210-217 (2010).
Stark Isolation, structure determination, synthesis and sensory activity of N-phenylpropenoyl L-amino acids from cocoa (*Theobroma cacao*) J agric Food Chem 53:5419-5428 (2005).
Reitz "Toward precision medicine in Alzheimer's disease" Ann Trans Med 4(6):107 (2016).
Stanford "Alzheimer's Prevention, Treatment and Research—A Q&A with Dr. Frank Longo" stanfordhealthcare.org/stanford-health-now/2016/alzheimers-prevention-treatment-research-qa-longo.html (accessed May 3, 2016 (2016).

(Continued)

*Primary Examiner* — Kathrien A Hartsfield
(74) *Attorney, Agent, or Firm* — TMB Law; Timothy M. Brown

(57) ABSTRACT

The invention provides a composition comprising one or more hydroxytryptamides and method of its use in the treatment of neurodegenerative disorders. The invention includes embodiments wherein the composition comprises caffeine and chlorogenic acids. The composition finds use in the treatment of Alzheimer's disease and Parkinson's disease, including providing neuroprotection against the advancement of the symptoms of these disorders.

22 Claims, 12 Drawing Sheets

(56) References Cited

OTHER PUBLICATIONS

Cho, J Med Food 16 (9) 20132, 823-830.
Stalmach, Food Funct., 2014, 5, 1727-1737.
Thom, The J of International Med Res, 2007, 35, 900-908.
Yowtak, Pain 152, 2011, 844-852.
Bagdas, Nat. Med. 2013, 67:698-704.
Narita, Biosci.Biotechnol. Biochem. 2012, 76 (15), 2329-2331.

* cited by examiner
COMPOSITION AND METHOD OF USING EICOSANOYL-5-HYDROXYTRYPTAMIDE FOR TREATING NEURODEGENERATIVE DISORDERS

CROSS-REFERENCE TO RELATED APPLICATIONS

This application claims the benefit of Provisional Application No. 62/903,800 filed Sep. 21, 2019, the entire contents of which are incorporated herein by reference for all purposes.

FIELD OF INVENTION

The invention relates to therapeutics and functional supplements for the treatment of neurodegenerative disorders.

BACKGROUND OF THE INVENTION

Neurodegenerative diseases are characterized by the progressive loss of a selective population of neurons due to protein abnormalities, oxidative stress, and neuroinflammation. Neurodegenerative diseases are generally categorized according to primary clinical features (e.g. parkinsonism and dementia) (Dugger & Dickson, 2017).

Alzheimer's disease is the most common form of dementia affecting older populations (Ghumatkar et al., 2015). Alzheimer's disease is a progressive neurodegenerative disease characterized by global cognitive decline (Tanzi & Bertram, 2005). Alzheimer's disease pathology involves formation of plaques rich in insoluble aggregates of beta-amyloid and neurofibrillary tangles in the brain (Kwon et al., 2010). Beta-amyloids interfere in the neuron-to-neuron communication at the synapses while tau tangles cause axonal transport dysfunction and neuronal loss (Ali et al., 2015; Alzheimer's Association, 2017). In addition, memory impairment is associated with cholinergic dysfunction due to loss of cholinergic neurons (Lee et al., 2015). A few studies have suggested that high oxidative stress can cause memory impairment, contributing to Alzheimer's disease pathology (Ding et al., 2007). Altogether, the available literature suggests that Alzheimer's disease is a result of multifactorial conditions and may benefit from a treatment strategy involving multiple targets.

Complementary and alternative medicine has emerged as a popular means of addressing several chronic diseases including neurological diseases (Parvez, 2018). Use of plants and herbal preparations in the treatment of neurodegenerative diseases is a promising alternative to synthetic drugs due to the presence of bioactive principles acting as specific inhibitors of therapeutic targets. Several small molecules from plant sources have been approved as natural drugs for the treatment of neurological disorders (Boll et al. 2011). These include opioids alkaloids (Pathan and Williams, 2012), galantamine (Olin and Schneider, 2002), and anticholinesterases like physostigmine and neostigmine (Colovic et al. 2013). Identification of small molecules in the plants which can bind specifically to their target proteins and modulate the cellular pathway of disease pathology is a critical step in the discovery of natural products for the treatment of neurodegenerative disorders such as Parkinson's disease (PD) and Alzheimer's disease.

Eicosanoyl-5-hydroxytryptamide (EHT) is a bioactive component of coffee unrelated to caffeine. EHT is a serotonin derivative wherein the C20 saturated fatty acid, eicosanoic acid, is linked to the serotonin amino group. The present invention provides an EHT composition derived from green coffee beans for the improvement of neuronal health and cognitive function.

SUMMARY OF THE INVENTION

An object of the invention is to provide a composition formulated from natural sources and methods for its use in the treatment of neurodegenerative disorders, such as Parkinson's disease and Alzheimer's disease. The invention is unique in its ability to target multiple targets of neurodegenerative disorders, including inhibiting acetylcholinesterase activity, increasing the activity and expression of brain-derived neurotrophic factor (BDNF), inhibiting Polo-like kinase 2 (Plk-2) and the accumulation of phosphorylated α-synuclein, and providing antioxidant protection against the free radical damage of neurons.

An object of the invention is to provide a composition for treating a neurodegenerative disease, comprising about 10% w/w EHT.

In at least one aspect of the invention, the composition comprises 10.17% w/w EHT.

In some aspects of the invention, the composition comprises about 0.40% w/w octadecanoic hydroxytryptamide, about 0.30% w/w heneicosanoic hydroxytryptamide, about 4.60% w/w docosanoic hydroxytryptamide, about 0.40% w/w tricosanoic hydroxytryptamide, about 0.90% w/w tetracosanoic hydroxytryptamide, and about 0.10% pentacosanoic hydroxytryptamide.

In some aspects of the invention, the composition comprises about 0.42% w/w octadecanoic hydroxytryptamide, about 0.27% w/w heneicosanoic hydroxytryptamide, about 4.55% w/w docosanoic hydroxytryptamide, about 0.39% w/w tricosanoic hydroxytryptamide, about 0.85% w/w tetracosanoic hydroxytryptamide, and about 0.06% pentacosanoic hydroxytryptamide, and said eicosanoic hydroxytryptamide is present in an amount of about 10.17% w/w.

In some aspects of the invention, the composition further comprises one or more chlorogenic acids selected from 3-CQA, 5-CQA, 4-CQA, 5-FQA, 3,4-diCQA, 3,5-diCQA, 4,5-diCQA.

In some aspects of the invention, the composition further comprises caffeine.

In some aspects, the invention provides a method of treating a neurodegenerative disorder, comprising administering to a patient in need thereof a composition of the invention as disclosed herein.

DETAILED DESCRIPTION

Figure 1A:
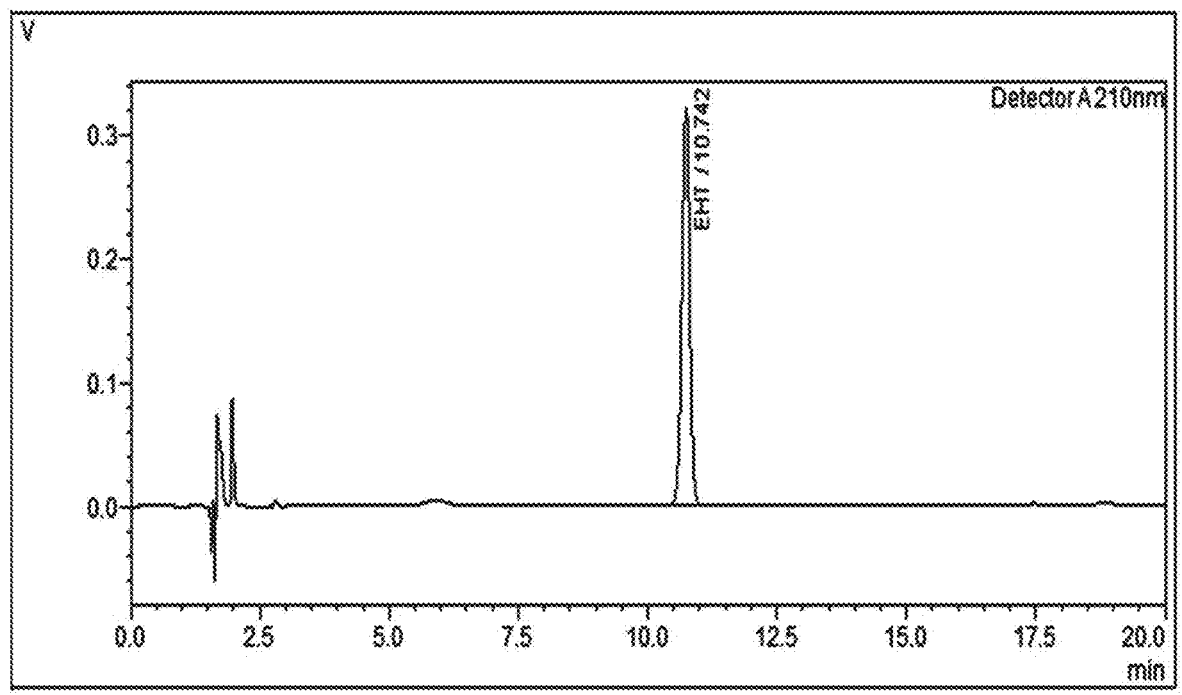
FIG. 1A shows an HPLC chromatogram of reference compound EHT.

The invention generally relates to natural drugs for the treatment of neurodegenerative disorders. More particularly, the invention relates to a composition comprising EHT and method for its use in the treatment of neurodegenerative disorders.

In at least one embodiment, the composition comprises between about 5% and about 20% EHT, by weight. In one non-limiting embodiment, the composition comprises between about 10% and about 12% EHT, by weight. The composition can comprise, by weight, about 5%, about 10%, about 15%, or about 20%. EHT. The term "about," as used herein, can mean the quantity, level, value, number, frequency, percentage, dimension, size, amount, weight or length that is referenced, or that varies (plus or minus) by as much as 30%, 25%, 20%, 15%, 10%, 9%, 8%, 7%, 6%, 5%, 4%, 3%, 2% or 1% of the referenced quantity, level, value, number, frequency, percentage, dimension, size, amount, weight or length. In some embodiments, the composition further comprises caffeine. It will be understood that all references to percentages in this description shall refer to the w/w percentage of the referenced compound or material, unless dictated otherwise by the context in which the percentage is used.

In some embodiments, the composition comprises EHT and at least one additional hydroxytryptamide. The composition can comprise EHT and one or more of octadecanoic hydroxytryptamide, heneicosanoic hydroxytryptamide, docosanoic hydroxytryptamide, tricosanoic hydroxytryptamide, tetracosanoic hydroxytryptamide, and pentacosanoic hydroxytryptamide.

In one non-limiting embodiment, the composition comprises about 10% EHT, about 0.40% w/w octadecanoic hydroxytryptamide, about 0.30% w/w heneicosanoic hydroxytryptamide, about 4.60% w/w docosanoic hydroxytryptamide, about 0.40% w/w tricosanoic hydroxytryptamide, about 0.90% w/w tetracosanoic hydroxytryptamide, and about 0.10% pentacosanoic hydroxytryptamide. The composition can comprise about 10.17% w/w EHT, about 0.42% w/w octadecanoic hydroxytryptamide, about 0.27% w/w heneicosanoic hydroxytryptamide, about 4.55% w/w docosanoic hydroxytryptamide, about 0.39% w/w tricosanoic hydroxytryptamide, about 0.85% w/w tetracosanoic hydroxytryptamide, and about 0.06% pentacosanoic hydroxytryptamide.

In some embodiments, the composition further comprises caffeine. The composition can have between about 0.5% and about 5% caffeine. In one non-limiting embodiment, the composition comprises about 1% w/w caffeine.

In some embodiments, the composition further comprises one or more chlorogenic acids. The chlorogenic acids can be, without limitation, one or more of 3-caffeoylquinic acid (3-CQA), 5-caffeoylquinic acid (5-CQA), 4-caffeoylquinic acid (4-CQA), 5-feruloylquinic acid (5-FQA), 3,4-dicaffeoylquinic acid (3,4-diCQA), 3,5-dicaffeoylquinic acid (3,5-diCQA), and 4,5-dicaffeoylquinic acid (4,5-diCQA). For example, the composition can comprise EHT, caffeine, and a mixture of chlorogenic acids comprising 3-CQA, 5-CQA, and 4-CQA. In some embodiments, the composition comprises a mixture of chlorogenic acids consisting of 3-CQA, 5-CQA, and 4-CQA. In other embodiments, the mixture comprises 3-CQA, 5-CQA, 4-CQA, 5-FQA, 3,4-diCQA, 3,5-diCQA, and 4,5-diCQA in a ratio of about 2.7:10.2:3.7:1.0:1.4:1.0:1.7, by weight. The mixture can consist of, by weight, about 12.5 w/w % 3-CQA, about 46.9 w/w % 5-CQA, about 17.2 w/w % 4-CQA, about 4.6 w/w % 5-FQA, about 6.2 w/w % 3,4-diCQA, about 4.6 w/w % 3,5-diCQA, and about 8.0 w/w % 4,5 di CQA.

In at least one embodiment, the composition further comprises at least one carrier, at least one excipient, or a combination thereof. The carriers and excipients can be selected on the basis of their compatibility with EHT and the other active components in the composition and the properties of the desired dosage form. The carrier or excipient can be an artificial carrier or excipient. Suitable excipients include, but are not limited to, binders, fillers, bulking agents, flow aids/glidents, disintegrants, lubricants, stabilizers, surfactants, or combinations thereof. Suitable excipients and carriers for use with the composition include, but are not limited to, those disclosed in: Remington: The Science and Practice of Pharmacy, 19$^{th}$ Ed (Easton, Pa.: Mack Publishing Company, 1995); Hoover, John E., Remington's Pharmaceutical Sciences, (Easton, Pa.: Mack Publishing Co 1975); Liberman, H. A. and Lachman, L., Eds., Pharmaceutical Dosage Forms (New York, N.Y.: Marcel Decker 1980); and Pharmaceutical Dosage Forms and Drug Delivery Systems, Seventh Ed (Lippincott Williams & Wilkins 1999). The entire contents of these publications are incorporated herein by reference for all purposes.

In some aspects of the invention, the composition employs controlled, sustained, or extended release formulations known collectively as "modified release" formulations. Modified release formulations can be selected from hydropropylmethyl cellulose, other polymer matrices, gels, permeable membranes, osmotic systems, multilayer coatings, microparticles, liposomes, microspheres, or combinations thereof.

At least one aspect of the invention concerns the dosage form of the composition. The composition can be in the form of a powder, liquid, pill, tablet, pellet, capsule, thin film, solution, spray, syrup, linctus, lozenge, pastille, chewing gum, paste, vapor, suspension, emulsion, ointment, cream, lotion, liniment, gel, drop, topical patch, buccal patch, bead, gummy, gel, sol, injection, or combinations thereof. The composition can be formulated for oral administration. The composition can be combined with vitamins, minerals, amino acids, proteins, extracts, carbohydrates, lipids, fatty acids, caffeine, flavorings, sweeteners, preservatives, or combinations thereof. In some embodiments, the composition is combined with a nutritional supplement, food supplement, or beverage. The composition can be formulated in bulk for use in the manufacture of nutritional supplements, food supplements, and beverages. Bulk formulations can be provided in containers, such as drums or bags, so as to inhibit the oxidation of the active components of the composition.

In some embodiments, the invention provides a method for making the composition. The method can be practiced by providing the components of the composition as disclosed herein, and combining the components. The components can be in isolated form. For example, the method can be practiced by combining one or more of isolated EHT (and one or more isolated hydroxytryptamides disclosed herein), isolated caffeine, and isolated chlorogenic acids to achieve the composition disclosed herein. In some non-limiting embodiments, the composition is made from an extract of a botanical material, such as, for example, green coffee beans, dried coffee beans, fully roasted coffee beans, partially roasted coffee beans, or combinations thereof. In some embodiments, the composition is made from an extract of coffee cherry, coffee cherry mucilage, or a combination thereof. Examples of suitable coffee beans, coffee cherries, and coffee cherry mucilage for making the composition include *Coffea Arabica*, *Coffea Robusta*, and the like. In some embodiments, the composition is extracted from coffee bean powder.

The composition can be made from the botanical material by a process selected from solvent extraction, extrusion, and a combination thereof. Suitable solvents for obtaining the composition include, but are not limited to, aqueous solvents, alcohol-based solvents, supercritical fluids, polar organic solvents (such as acetone and methylethyl ketone), or combinations thereof. Non-limiting examples of alcohol-based solvents include, but are not limited to, ethanol, isopropyl alcohol, methanol, or combinations thereof. The composition can be extracted by supercritical fluid extraction. The supercritical fluid can be, but is not necessarily limited to, carbon dioxide. In one non-limiting embodiment, the composition is extracted from a powder of green coffee beans, wherein the powder is sprayed with at least one of ethyl alcohol, methanol and isopropyl alcohol, and subjected to super critical fluid extraction with carbon dioxide.

The invention further provides a method of treating a neurodegenerative disorder. As used herein, the terms "treat," "treating," "treatment," and the like can refer to the clinical intervention of a neurodegenerative disorder or condition in an attempt to alter, alleviate, ameliorate, prevent, lessen or reverse the progression or symptoms of the neurodegenerative disorder or condition.

In at least one embodiment, the method is practiced by administering a composition as disclosed herein to a patient (e.g. a human patient) in need of treatment for a neurodegenerative disorder. In some aspects of the invention, the neurodegenerative disorder is Alzheimer's disease. The Alzheimer's disease can present as mild cognitive impairment, Creutzfeldt-Jakob disease, dementia with Lewy bodies, vascular dementia, alcohol-related brain damage, young-onset dementia, frontotemporal dementia, HIV-related cognitive impairment, or a combination thereof. The patient can have Alzheimer's disease, or be at risk of developing Alzheimer's disease. In some aspects of the invention, the presence Alzheimer's disease is indicated by symptoms of Alzheimer's disease (e.g. cognitive impairment or decline) or one or more biological markers for the disease, including cerebrospinal fluid levels of total Tau protein, phosphorylated Tau, and beta-amyloid peptide as known in the art. In some aspects of the invention, the patient can be at risk of developing Alzheimer's disease, as indicated by the patient's age, patient lifestyle (e.g. alcohol consumption or diet), or familial history. In at least one embodiment, the patient has early Alzheimer's disease as indicated by a combination of low beta-amyloid peptide and high levels of total Tau and phosphorylated Tau proteins.

Administering the composition can treat the symptoms of Alzheimer's disease. For example, administering the composition to a patient with Alzheimer's disease can inhibit at least one of cognitive decline and memory impairment. In some aspects, administering the composition to a patient with Alzheimer's disease improves at least one of cognitive function and memory. In still other aspects, administering the composition to a patient with Alzheimer's disease treats the underlying physiopathology of the disease. For example, administering the composition can inhibit increases in neurofibrillary tangles, amyloid pathologies, total Tau, phosphorylated Tau, and beta-amyloid peptide.

In some aspects of the invention, the method inhibits the development of symptoms of the disease in a patient at risk of developing Alzheimer's disease. For example, administering the composition can inhibit cognitive decline and memory impairment in a patient at risk of developing Alzheimer's disease. In other aspects, the method inhibits the progression of the pathophysiology of the disease in a patient at risk of developing Alzheimer's disease. For example, administering the composition can inhibit the formation of neurofibrillary tangles, inhibit the formation of amyloid pathologies, inhibit increases in at least one of total Tau, phosphorylated Tau, and beta-amyloid peptide, or combinations thereof. Thus, administering the composition of the invention can provide a neuroprotective effect to a patient at risk of developing Alzheimer's disease.

Without being limited to any particular theory or mechanism, administering the composition of the invention treats Alzheimer's disease by targeting multiple disease targets, including one or more of inhibiting acetylcholinesterase activity, increasing the activity or expression of brain-derived neurotrophic factor (BDNF), and providing antioxidant protection against neuronal cell damage by free radicals.

In at least one embodiment, the invention provides a method of treating Parkinson's disease in a patient in need thereof, comprising administering to the patient a composition as disclosed herein. The patient can have, or be at risk of developing, Parkinson's disease. In some aspects of the invention, the method is practiced by administering to the patient a composition comprising about 10% EHT, caffeine, and a mixture of chlorogenic acids comprising or consisting of 3-CQA, 4-CQA, and 5-CQA. Without being limited to any particular theory or mechanism, the invention treats Parkinson's disease by inhibiting the activity of Polo-like kinase 2 (Plk-2) thereby preventing or inhibiting the accumulation of phosphorylated α-synuclein protein.

At least one aspect of the invention concerns the administration of the composition. The composition can be administered to the patient systemically. Suitable administration routes for the composition include, but are not limited to, auricular, buccal, conjunctival, cutaneous, dental, endocervical, endosinusal, endotracheal, enteral, epidural, extra-amniotic, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal dental, intracoronary, intracorporus cavernosum, intradermal, intradiscal, intraductal, intraduodenal, intradural, intraepidermal, intraesophageal, intragastric, intravaginal, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravitreal, laryngeal, nasal, nasogastric, ophthalmic, oral, oropharyngeal, parenteral, percutaneous, periarticular, peridural, perineural, periodontal, rectal, inhalation, retrobulbar, soft tissue, subarachnoid, subconjunctival, subcutaneous, sublingual, submucosal, topical, transdermal, transmucosal, transplacental, transtracheal, transtympanic, ureteral, urethral, vaginal, or combinations thereof. The composition can be administered by irrigation, drip, infusion, or topically by a dressing, patch, or bandage that is in contact with the composition.

Another aspect of the invention concerns the dosage of the composition. The composition can be administered at a dose of between about 50 mg/kg and about 600 mg/kg. It will be understood that "mg/kg" as used herein refers to milligrams of the composition per kilogram body weight of the patient. The composition can be administered at a dose of between about 200 mg/kg and about 400 mg/kg. The composition can be administered at a dose of about 50 mg/kg, about 100 mg/kg, about 150 mg/kg, about 200 mg/kg, about 250 mg/kg, about 300 mg/kg, about 350 mg/kg, about 400 mg/kg, about 450 mg/kg, about 500 mg/kg, about 550 mg/kg, or about 600 mg/kg as well as any dosage intervening two of these specifically disclosed dosages. The composition can be administered one, two, three, four, five, six, seven, or more times daily, weekly, or monthly. The composition can be administered multiple times wherein the doses are the same or a combination of the doses disclosed herein.

Example 1: Preparation of the Composition

The extraction process described in the present invention can be scaled up to produce larger quantities of extract.

Step 1: 100 kg of 2-3 mm size green coffee bean powdered raw material was taken into a 5-micron polypropylene cloth and sprayed with 5 L of ethyl alcohol, methanol or isopropyl alcohol as a co-solvent. The cloth was tied well and put it into a clean, dry supercritical fluid extractor. Extraction was started at 60-65° C. by passing $CO_2$ gas under 300 Bar pressure for about 4-6 h. The resulting oleoresin (oil) was collected in receiver tank and residual moisture removed under vacuum at 60-65° C. in a clean reactor under stirring. Weight of the oleoresin (oil) was about 10-12 kg. Content of EHT in the oleoresin was 0.5±0.1 w/w %.

Step 2: 100 L of solvents like n-Hexane, petroleum ether or heptane was into a 0.5-1.0 KL capacity reactor. About 10-12 kg of the oleoresin from Step 1 was slowly added into the reactor under stirring at room temperature. The stirring was continued for about half an hour and the precipitate was allowed to settle in a clean carboy at −5 to −10° C. for about 24-36 hours in a cold room. The top layer was decanted, and the precipitate filtered in a nutch filter and suck dried. The precipitate was dried thoroughly in a vacuum tray drier at 55-60° C. for about 8-10 h. Weight of the extract was about 1.0-1.3 kg and the EHT content 4.5-5.5 w/w %.

Step 3: 20-25 L of ethanol, isopropyl alcohol, ethyl acetate or acetone was charged into a clean 0.5 KL capacity reactor and 2-2.5 kg of the Step 2 extract was slowly added to a reactor under stirring. Stirring was continued for about a half an hour at 40-45° C. and filtered using a suitable filtering aid and sucked dry. The filtrate was collected and concentrated under vacuum until dry. Weight of the final extract was 0.5±0.1 kg and the EHT content was 10-12 w/w %. The final extract was used in the following examples. The final extract is referred to herein as Cervoffe.

Example 2: Quantification of EHT by High Performance Liquid Chromatography (HPLC)

Quantitative analysis of EHT in Cervoffe was determined using HPLC using the chromatographic conditions of Table 1.

TABLE 1

| HPLC Parameters | |
|---|---|
| Mobile phase A | 0.2% Formic acid |
| Mobile phase B | Acetonitrile |
| Column | XBC-18, 5 μm, 100 A°, 250 × 4.6 mm Phenomenex (Kinetex). |
| System | LC 2030 C Prominence-i |
| Flow rate | 1.5 ml/min |
| Volume of injection | 10 μl |
| Run time | 20 min |
| Wavelength | 210 nm |
| Oven temperature | 25° C. |
| Elution | Isocratic (A:B) (10:90) |
| Diluent | Methanol |

Standard Preparation

Accurately weighed 25.0 mg of EHT reference standard was taken in a 25 mL standard volumetric flask and dissolved in methanol to obtain a final concentration of 1,000 ppm. The standard solution was filtered through a 0.2μ nylon syringe filter and injected.

Sample Preparation

Weighed accurately around 25 mg of sample in to 25 mL volumetric flask, dissolved by adding methanol, sonicated and made up to the volume with methanol to get a final concentration in the range of 1,000 ppm. The sample solution was filtered through 0.2μ nylon syringe filter and injected.

Calculation $$\text{Assay \%} = \frac{\text{Peak area of the sample} \times \text{Conc. of the STD} \times \text{purity of the STD}}{\text{Peak area of the standard} \times \text{Conc. of the sample}}$$

Figure 1B:
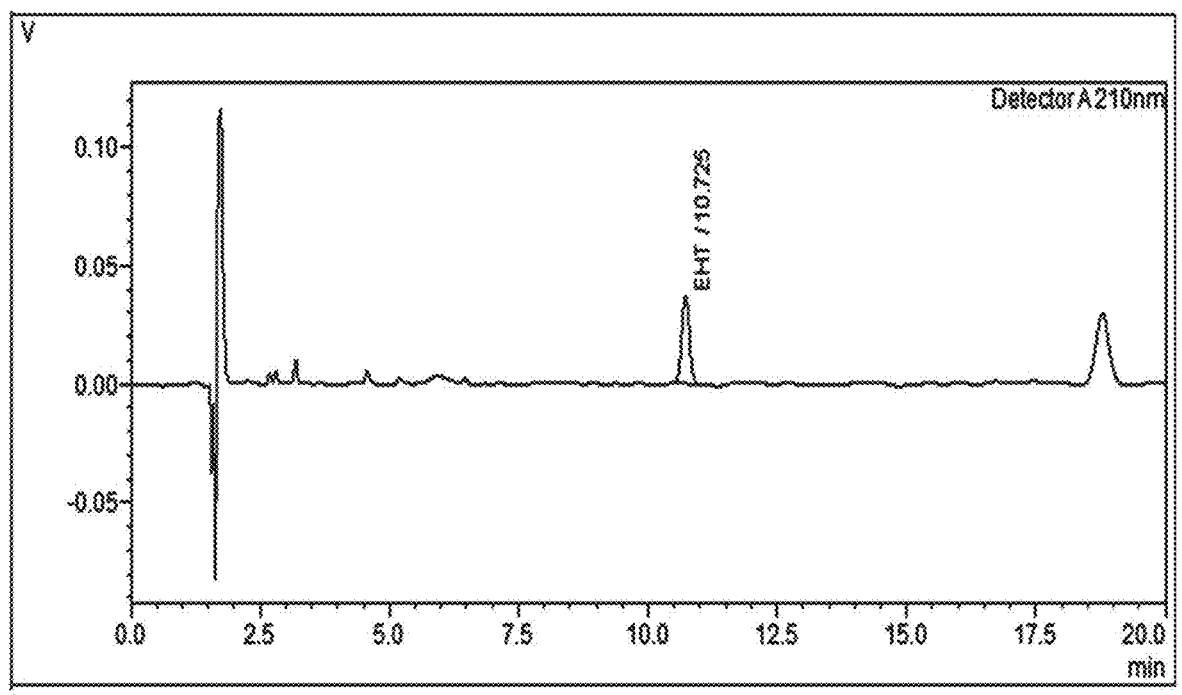
FIG. 1B shows an HPLC chromatogram of EHT from an embodiment of the inventive composition.

The retention time of reference standard EHT and sample peak were found to be at 10.742 and 10.725, respectively. The HPLC analysis showed the presence of 10% of EHT in Cervoffe. The spectral details of HPLC analysis are presented in FIGS. 1A and 1B.

Qualitative Analysis of EHT by Liquid Chromatography Mass Spectrometry (LCMS)

Qualitative analysis of EHT in Cervoffe was determined using LCMS using the chromatographic conditions of Table 2.

TABLE 2

Qualitative Analysis of Composition

| | |
|---|---|
| Mobile phase A | 0.2% Formic acid |
| Mobile phase B | Methanol |
| Column | C18, Kinetex (100 A°, 150 × 2.1 mm, 2.6 µm) |
| System | LC-MS/MS 8050 |
| Method | Isocratic (A:B) (10:90) |
| LC Time | 10.0 min |
| Flow rate | 0.25 ml/min |
| Injection volume | 5.0 µL |
| Column Temperature | 40° C. |
| Diluent | Methanol |
| Dissolvation line temperature | 250° C. |
| Nebulizing gas flow | 3.0 l/min |
| Heat block temperature | 400° C. |
| Interface temperature | 300° C. |
| Drying gas flow | 10.0 l/min |
| Heat gas flow | 10.0 l/min |
| MRM EVENT | +VE Ionization Mode |
| MRM Transitions | 471.2 > 160.0, 115.1, 132.2 |

Figure 2A:
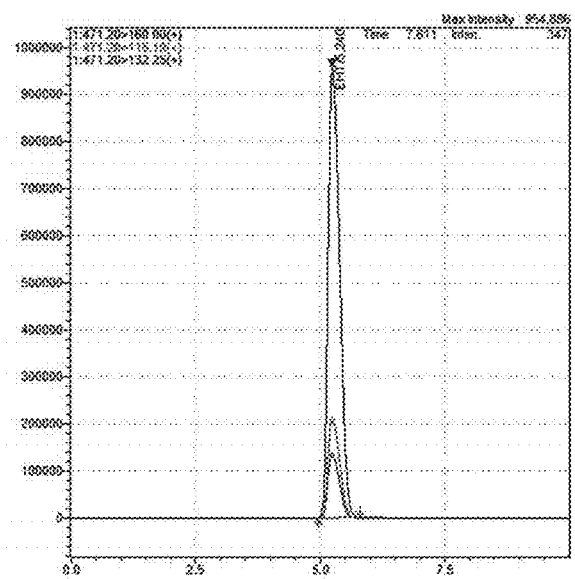
FIG. 2A shows the multiple reaction monitoring (MRM) chromatogram of reference compound EHT.
Figure 2B:
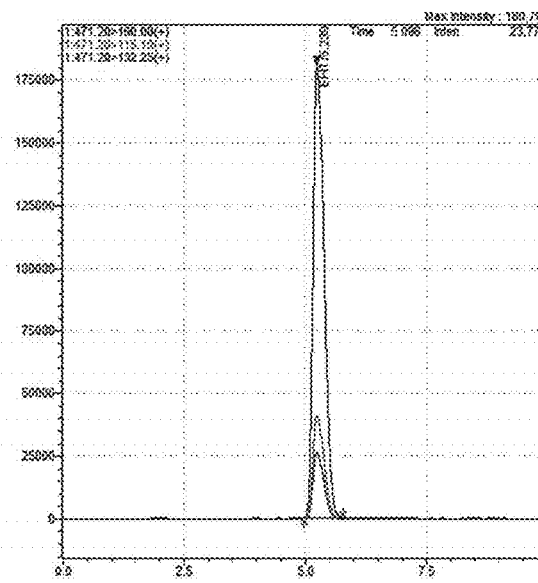
FIG. 2B shows the multiple reaction monitoring (MRM) chromatogram of EHT in an embodiment of the inventive composition.

The multiple reaction monitoring (MRM) chromatogram of the EHT standard is overlaid with Cervoffe MRM chromatogram qualitatively. The EHT standard and Cervoffe showed a $[M+H]^+$ peak at 471.20. The corresponding MS2 product (fragment) ions of standard and sample is 160.0, 115.0 and 132.25 (FIG. 2).

Example 3: Quantitative Analysis of Hydroxytryptamide Species

Materials

All reagents and solvents used in the study were of analytical and LC-MS grade. Octadecanoic hydroxytryptamide (88%), Eicosanoic hydroxytryptamide (92%), Heneicosanoic hydroxytryptamide (87%), Docosanoic hydroxytryptamide (98%), Tricosanoic hydroxytryptamide (95%), Tetracosanoic hydroxytryptamide (98%), Pentacosanoic hydroxytryptamide (98%) were used as a standard. The purity of the standards was >85%, which was quantified by HPLC.

Instrumentation and Chromatographic Conditions

Total hydroxytryptamide was quantified using triple quadrupole mass spectrometry (LC-MS/MS-8050, Shimadzu, Japan) equipped with electrospray ionization (ESI) source operating in positive ionization mode. Nitrogen was used as nebulizer, drying and heating gas. Argon gas was used for the collision induced dissociation (CID) gas. The separation was carried out in Kinetex C18 column (100 Å, 2.6 µm, 150×2.1 mm,) at a flow rate of 0.5 ml/min in ESI source. The mobile phase consisted of 0.2% formic acid: acetonitrile (A:B)=10:90 with isocratic elution and the injection volume of 2.5 µl. All solutions were degassed and filtered through 0.2 µm pore size filter. The column was maintained at 40° C. throughout analysis. Pure methanol was used as a diluent and the total run time was 10 min. The MS chromatographic conditions used in the study as follows: nebulizer gas flow, 3.0 L/min; drying gas flow, 10.0 L/min and heating gas flow, 10.0 L/min. The interface voltage and CID gas pressure were set at 3 Kv and 270 kPa. The interface temperature was maintained at 300° C., while desolvation line (DL) and heat block (interface) temperature were maintained at 250° C. and 400° C. respectively in ESI source. Quantification was performed by multiple reaction monitoring (MRM) method of protonated precursor ions and related product ions were as follows: the protonated ions $[M+H]^+$ at m/z 443.30→160.05 ion as a quantifier, 443.30→132.05 ion as a qualifier-1 and 443.30→115.10 ion as a qualifier-2 for octadecanoic hydroxytryptamide; $[M+H]^+$ at m/z 471.30→160.10 ion as a quantifier, 471.30→177.20 ion as a qualifier-1 and 471.30→132.05 ion as a qualifier-2 for eicosanoic hydroxytryptamide; $[M+H]^+$ at m/z 485.30→160.00 ion as a quantifier, 485.30→177.05 ion as a qualifier-1 and 485.30→132.10 ion as a qualifier-2 for heneicosanoic hydroxytryptamide; $[M+H]^+$ at m/z 499.30→160.00 ion as a quantifier, 499.30→177.10 ion as a qualifier-1 and 499.30→132.05 ion as a qualifier-2 for docosanoic hydroxytryptamide; $[M+H]^+$ at m/z 513.30→160.10 ion as a quantifier, 513.30→177.10 ion as a qualifier-1 and 513.30→132.15 ion as a qualifier-2 for tricosanoic hydroxytryptamide; $[M+H]^+$ at m/z 527.40→160.00 ion as a quantifier, 527.40→177.00 ion as a qualifier-1 and 527.40→132.15 ion as a qualifier-2 for tetracosanoic hydroxytryptamide; $[M+H]^+$ at m/z 541.10→160.00 ion as a quantifier, 541.10→177.05 ion as a qualifier-1 and 541.10→500.30 ion as a qualifier-2 for pentacosanoic hydroxytryptamide. Peak identification was based on the retention time and the sample ion chromatograms must fully overlap with the standard. The MS data processed by LabSolutions software.

Preparation of Standard Solutions

Accurately weighed 5.0 mg of each individual octadecanoic hydroxytryptamide, tricosanoic hydroxytryptamide, tetracosanoic hydroxytryptamide and pentacosanoic hydroxytryptamide standards separately in 10 ml volumetric flask and dissolved in methanol to obtain a stock concentration of 500 ppm. Ten mg of eicosanoic hydroxytryptamide, heneicosanoic hydroxytryptamide, docosanoic hydroxytryptamide, tricosanoic hydroxytryptamide, tetracosanoic hydroxytryptamide and pentacosanoic hydroxytryptamide standards were taken separately in 10 ml volumetric flask and dissolved in methanol to obtain a stock concentration of 1000 ppm.

Working standard solutions was obtained by diluting the 1.0 ml standard stock solution to 100 ml in volumetric flask and made up with methanol. Standard solution was filtered through 0.2µ nylon syringe filter and injected.

Preparation of Sample Solution

Weighed accurately around 20.0 mg of a sample prepared according the Example 1 into a 50 ml volumetric flask, dissolved by adding methanol, sonicated and make up to the volume with methanol to get a final concentration in the range of 400 ppm. Sample solution was filtered through 0.2µ nylon syringe filter and injected.

Calculation $$\text{Assay \%} = \frac{\text{Peak area of the sample} \times \text{Conc. of the STD} \times \text{purity of the STD}}{\text{Peak area of the standard} \times \text{Conc. of the sample}}$$

TABLE 3

| Qualitative Analysis of Composition | |
| --- | --- |
| Hydroxytryptamide | Assay Percentage (% w/w) |
| Octadecanoic hydroxytryptamide | 0.42 |
| Eicosanoic hydroxytryptamide | 10.17 |
| Heneicosanoic hydroxytryptamide | 0.27 |
| Docosanoic hydroxytryptamide | 4.55 |
| Tricosanoic hydroxytryptamide | 0.39 |
| Tetracosanoic hydroxytryptamide | 0.85 |
| Pentacosanoic hydroxytryptamide | 0.06 |

Example 4: Neuroprotection in the Animal Model of Alzheimer's Disease—Scopolamine-Induced Amnesia in Mice Cervoffe (10% EHT) was evaluated for neuroprotective effect in scopolamine-induced Alzheimer's disease-like condition in mice. The extract was dissolved in 0.5% carboxymethyl cellulose for animal experiments.

Materials and Methods

Animals

Healthy male Swiss albino mice (6-8 weeks) were used in this study. The animals were procured from authorized suppliers of laboratory animals—Biogen, Bangalore, India (Reg No. 971/PO/RcBiBt/S/2006/CPCSEA). The animals were placed in polypropylene cages and housed in a room under controlled atmosphere (temperature, 22±3° C., humidity, 30-70%; 12 h light/dark cycle). During the seven days acclimatization period, all mice consumed a commercial diet and tap water ad libitum. The animal studies were performed after due clearance from the Institutional Animal Ethics Committee independently formed by CPCSEA (Committee for the purpose of control and supervision of experiments on animals, a statutory committee established under the Prevention of Cruelty to Animals Act, 1960 in India).

Experiment Design

Mice were divided into five groups (n=6 per group); Group I—normal control, Group II disease control (scopolamine hydrobromide 1 mg/kg, i.p.), Group III—standard treatment (scopolamine+donepezil hydrochloride 3 mg/kg, p.o.), Group IV—Scopolamine+Cervoffe (200 mg/kg, p.o.), and Group V—scopolamine+Cervoffe (400 mg/kg, p.o.). Groups III-V mice were dosed every 24 h interval with respective drugs for 7 consecutive days. On day 7, amnesia was induced in all the groups except the control group by intraperitoneal injection of scopolamine (1 mg/kg) 30 minutes after the respective treatments. 30 minutes later, elevated plus maze (EPM) was carried out to assess the cognitive function. At the end of experiment, mice were sacrificed; serum and brain homogenates were used for further analysis.

Behavioral Screening—Elevated Plus Maze

EPM was performed by the method of Vijayalakshmi et al. (2012) with slight modifications. Briefly, the acquisition trail (day 6) was carried out by placing the mouse at the end of an open arm. The time taken by the mouse to enter any of the closed arms was taken as transfer latency. Cutoff time allotted for each mouse was 180 s. Retention trail was carried out 24 h after the first trail (Day 7, 30 min after scopolamine treatment). The transfer latency was determined in a similar manner as mentioned before. Shortened transfer latency was considered as an index of memory improvement.

Determination of Acetylcholinesterase (AchE) Activity in Brain

AchE in the brain homogenates of mice was estimated using the method of Ellman et al. (1961). The rate of moles of substrate hydrolyzed per milligram of protein was calculated.

Measurement of Brain Derived Neurotrophic Factor (BDNF)

The BDNF level in brain homogenates was measured using a commercial kit (RayBiotech, Inc. USA). Briefly, 100 µL samples were pipetted into wells pre-coated with an antibody specific for BDNF and incubated for 2.5 h at room temperature. The wells were washed 4 times with wash buffer and 100 µL of biotinylated anti-BDNF antibody was added and incubated for 1 h at room temperature. The wells were washed and 100 µL of HRP-conjugated streptavidin solution was added to each well and incubated for 45 min at room temperature. The wells were again washed, a TMB substrate solution was added to the wells and incubated for 30 min. at room temperature in the dark. After incubation, 50 nt of stop solution was added to each well and absorbance was immediately read at 450 nm.

Determination of Lipid Peroxidation

Lipid peroxidation in the brain homogenates was measured by estimating the formation of thiobarbituric acid reactive substances (TBARS). Malondialdehyde (MDA) is an end product of lipid peroxidation, which reacts with thiobarbituric acid to form a pink chromogen thiobarbituric acid reactive substance (Ohkawa et al., 1979). The reaction mixture contained 0.2 mL of liver homogenate, 0.2 mL of 8% sodium dodecyl sulphate, 3.0 mL of 0.8% thiobarbituric acid in 20% acetic acid and the solution was made up to 4.0 mL using distilled water. The solution was incubated at 95° C. in a water bath for 60 min. After incubation, the solution was cooled, and absorbance was measured at 532 nm. Total TBARS were expressed as MDA, using a molar extinction coefficient for MDA of $1.56 \times 10^5$ $cm^{-1}M^{-1}$. Results were expressed as nmol MDA/mg protein.

Glutathione Assay

GSH levels were determined by the method of Ellman (1959) with slight modification. Briefly, 200 µL of brain homogenate was mixed with 100 µL of 10 mM Ellman's reagent. The volume was made up to 1 mL using 0.1 M phosphate buffer with 5 mM EDTA, pH 7.4 and the yellow color that developed was read at 412 nm. The concentration of GSH in the sample was determined by calculating from the linear equation or the regression curve generated from GSH standard.

Histopathological Examination

The brain tissue samples were fixed in 4% formalin, dehydrated with a graded alcohol series, embedded in paraffin, and then cut into 4 µm thickness slices. The sections were stained with hematoxylin and eosin (H&E, Sigma-Aldrich, St. Louis, MO, USA). The images were captured using a microscope (Leica, Germany).

Western Blot Analysis

The brain tissue from each animal was homogenized in lysis buffer and incubated for 20 minutes to induce cell lysis. Tissue extracts were centrifuged at 12,000 rpm for 20 minutes and the supernatants were transferred to clean tubes. Aliquots of protein samples (75 µg) were resolved on 10-15% sodium dodecyl sulphate-polyacrylamide gel electrophoresis gels and transferred onto a nitrocellulose membrane. The membranes were incubated for 1 hr with blocking solution and subsequently incubated with 1:500 dilution of primary antibodies, including anti-BDNF and anti-TrkB overnight at 4° C. The membranes were washed three times with 0.1% Tween 20 in TBS followed by incubation with Horseradish peroxidase conjugated goat IgG antibody (1:4000 dilution) for 1 h at room temperature. Detection was performed on ImageQuant™ LAS 500 (GE Healthcare Life Sciences). GAPDH was used as a loading control.

Behavioral Analysis

Figure 3:
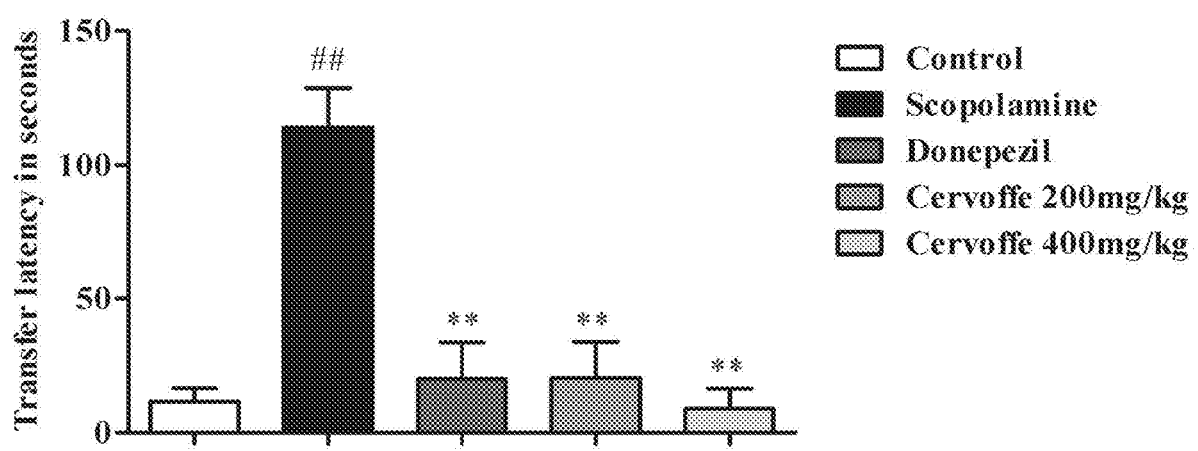
FIG. 3 shows the effect of an embodiment of the inventive composition on behavior in scopolamine-induced amnesia in mice in an elevated plus maze analysis.

In this study, EPM was applied as a behavioral model to assess learning and memory. EPM is used to study long term spatial memory (Uddin et al. 2016). A decrease in transfer latency indicates improvement in memory (Dhingra & Kumar, 2012). In the EPM screening test, 1 mg/kg scopolamine significantly increased the transfer latency of mice compared to normal control ($p<0.001$). A 7-day pre-treatment of mice with donepezil or respective doses of Cervoffe (200 and 400 mg/kg) significantly reduced the latency period by 82.45%, 82.02% and 92.1% respectively compared to scopolamine control group ($p<0.001$). Findings obtained from the EPM test are illustrated in FIG. 3.

Effect of Cervoffe on AchE Levels in Brain Homogenate

Figure 4A:
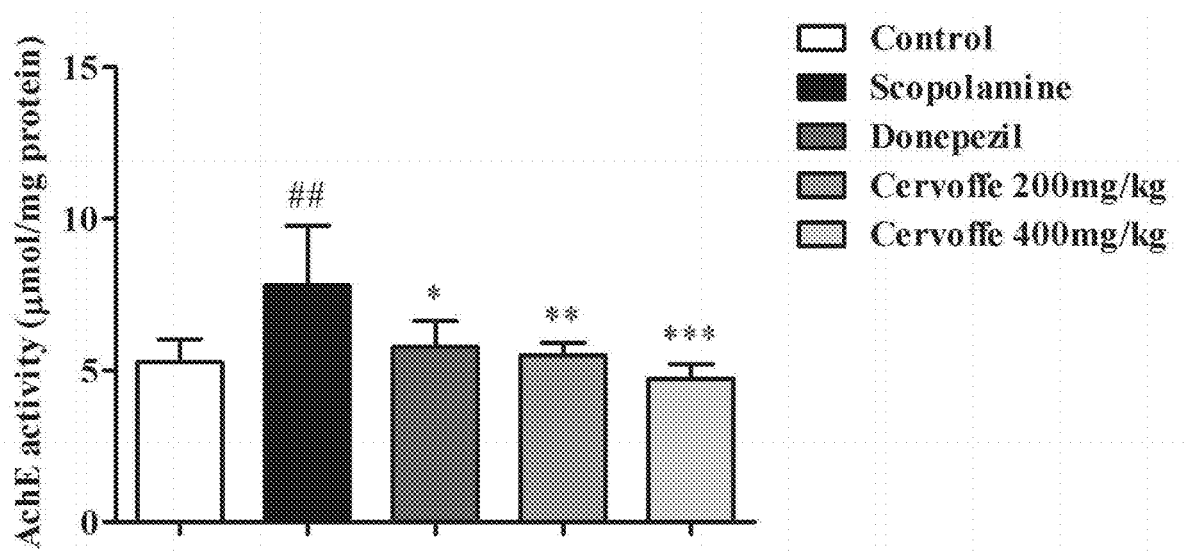
FIG. 4A shows the effect of an embodiment of the inventive composition on acetylcholinesterase (AchE) activity in scopolamine-induced amnesia mice.

A single intraperitoneal administration of scopolamine significantly increased the activity of AchE (7.8±1.97; $p<0.01$) when compared to normal group (5.27±0.75). Pretreatment of mice with 200 mg and 400 mg/kg of Cervoffe dose-dependently reduced the AchE activity (5.5±0.4 and 4.72±0.48 respectively). Oral administration of donepezil and low dose and high dose of Cervoffe significantly decreased the AchE activity in mice brain by 26.02% ($p<0.05$), 29.48% ($p<0.01$) and 39.48% ($p<0.001$) respectively as compared to the scopolamine-treated group (FIG. 4A). One of the promising strategies to treat cognitive deficit in Alzheimer's disease is to improve the cholinergic function and inhibit the AchE activity (Agrawal et al. 2009). In this study, Cervoffe markedly decreased the AchE activity, which in turn increases the availability of acetylcholine for improving cognitive function.

Effect on BDNF Levels in the Brain

Figure 4B:
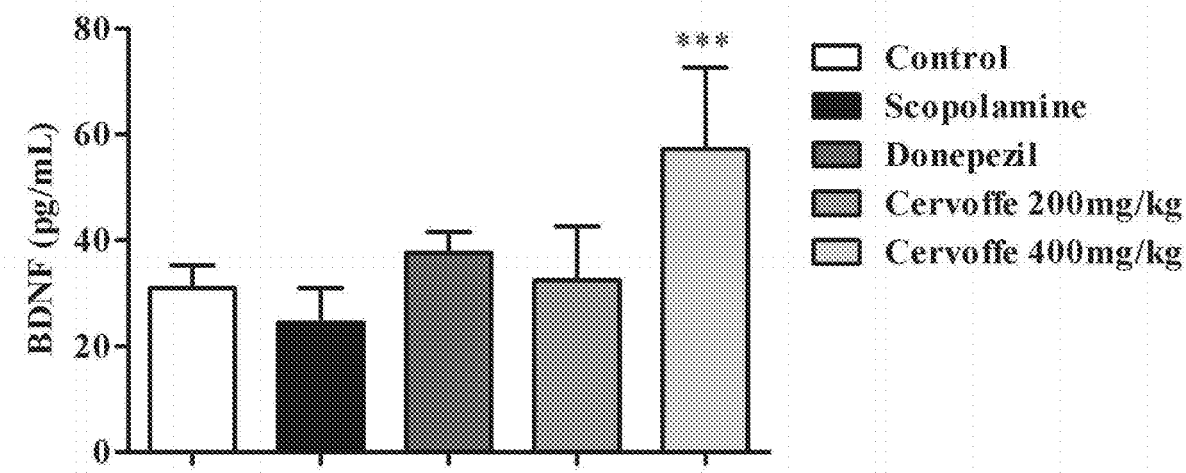
FIG. 4B shows the effect of an embodiment of the inventive composition on the levels of BDNF in mice brain determined by ELISA.

BDNF levels were markedly reduced in brain homogenates of the scopolamine group, compared with normal group ($p<0.05$). However, this reduction was ameliorated by the low and high doses of Cervoffe in a dose-dependent manner (FIG. 4B). In comparison with the scopolamine control, a significant increase in the BDNF level was observed for the 400 mg/kg Cervoffe treatment group ($p<0.001$).

Effect on Lipid Peroxidation and Reduced Glutathione in the Brain

Figure 5A:
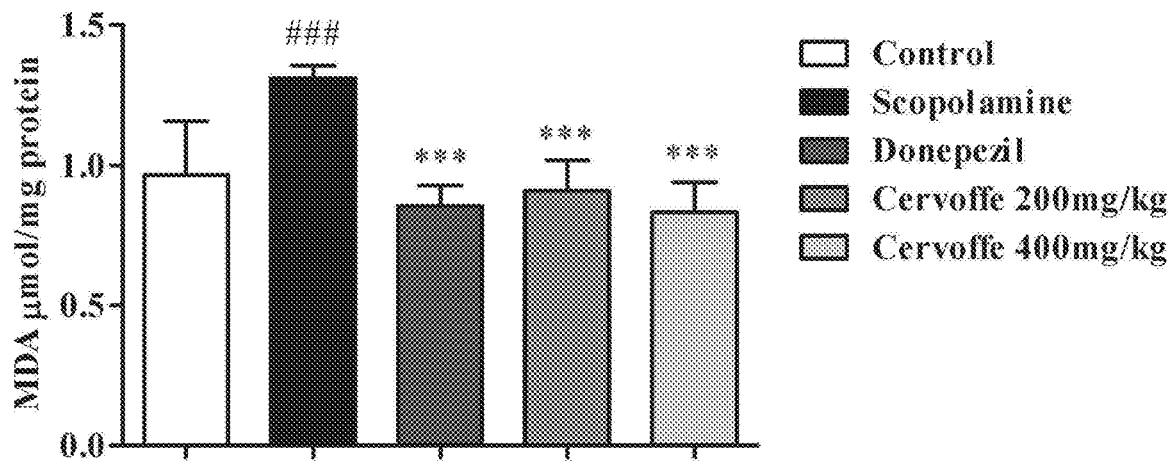
FIG. 5A shows the effect of an embodiment of the inventive composition on lipid peroxidation in mice.

Neurodegenerative diseases are characterized by oxidative damage due to the imbalance between the generation of free radicals and the antioxidant defense system. In this study, MDA levels, as a measure of lipid peroxidation, was elevated significantly in scopolamine-induced amnesia mice as compared to normal control ($p<0.001$). 200 mg/kg and 400 mg/kg doses of Cervoffe significantly reversed the oxidative damage ($p<0.001$) compared to untreated scopolamine-induced mice (FIG. 5A).

Figure 5B:
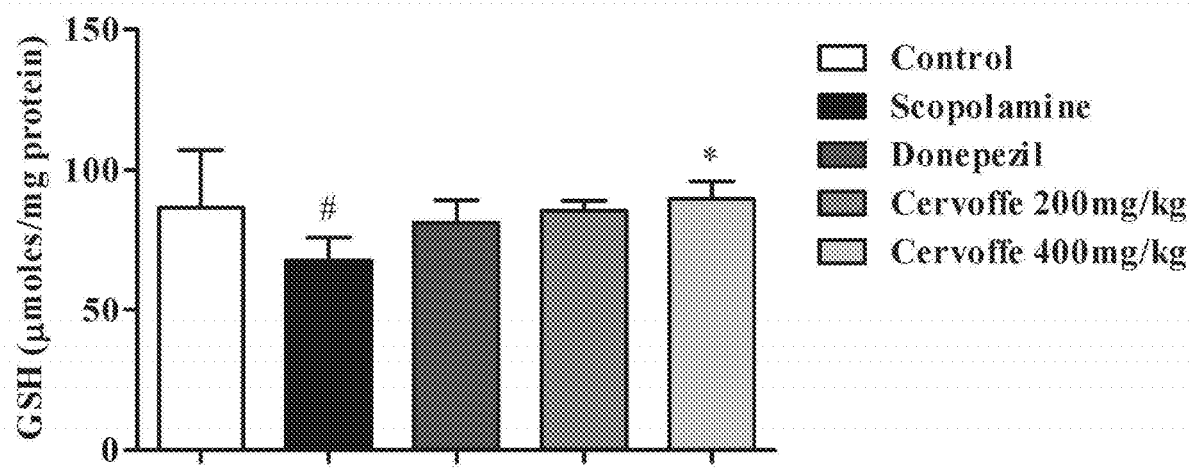
FIG. 5B shows the effect of an embodiment of the inventive composition on reduced glutathione (GSH) level in mice.

Scopolamine-induced mice showed considerable decrease in reduced GSH levels ($p<0.05$; 67.66±8.31) as compared to the normal group (86.52±20.56). Pre-treatment with low and high doses of Cervoffe dose-dependently improved the brain GSH levels in the scopolamine-induced mice (FIG. 5B). 400 mg/kg dose of Cervoffe significantly increased the reduced GSH levels as compared to untreated amnesia mice ($p<0.05$; 89.85±6.14).

Histological Alterations in Brains of Scopolamine-Induced Mice

Figure 6A:
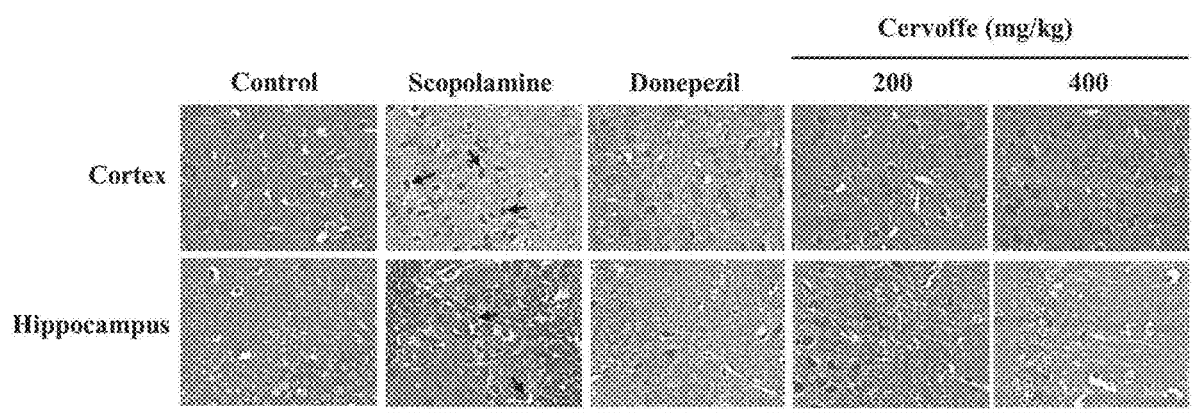
FIG. 6A shows the effect of an embodiment of the inventive composition on brain histomorphology of scopolamine-induced mice.
Figure 6B:
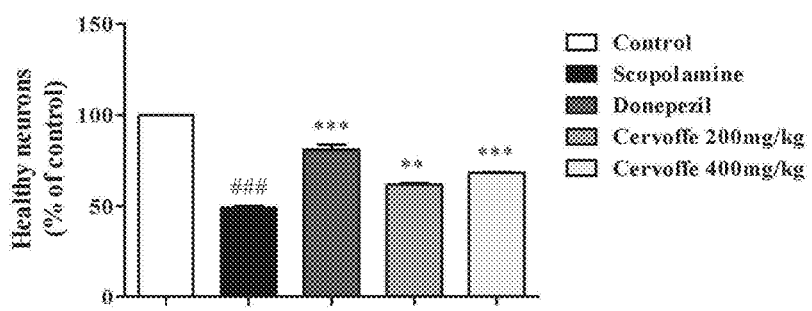
FIG. 6B shows the effect of an embodiment of the inventive composition on neuron health in scopolamine-induced mice.

The brain tissues of scopolamine-treated mice showed unhealthy neurons (indistinct, shrunken and possessing a darkened nucleus). Administration of low and high dose of Cervoffe restored the normal architecture of brain tissue (FIG. 6A). There was a significant reduction in the number of healthy neurons in brain hippocampus region of scopolamine-induced mice as compared to control group ($p<0.001$). However, pretreatment with Cervoffe (200 mg and 400 mg/kg) and donepezil significantly improved the healthy neurons as compared to untreated amnesia mice ($p<0.001$) (FIG. 6B).

Effect on BDNF-TrkB Signaling in Brain

Figure 7:
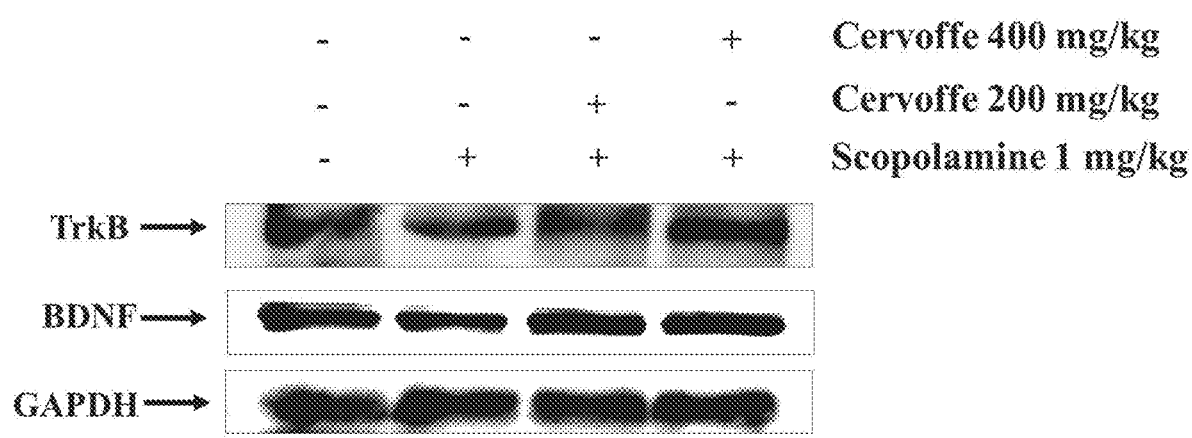
FIG. 7 shows the Western blot analysis for the expression of BDNF and TrkB proteins in brain homogenates of scopolamine-induced mice.
Figure 8:
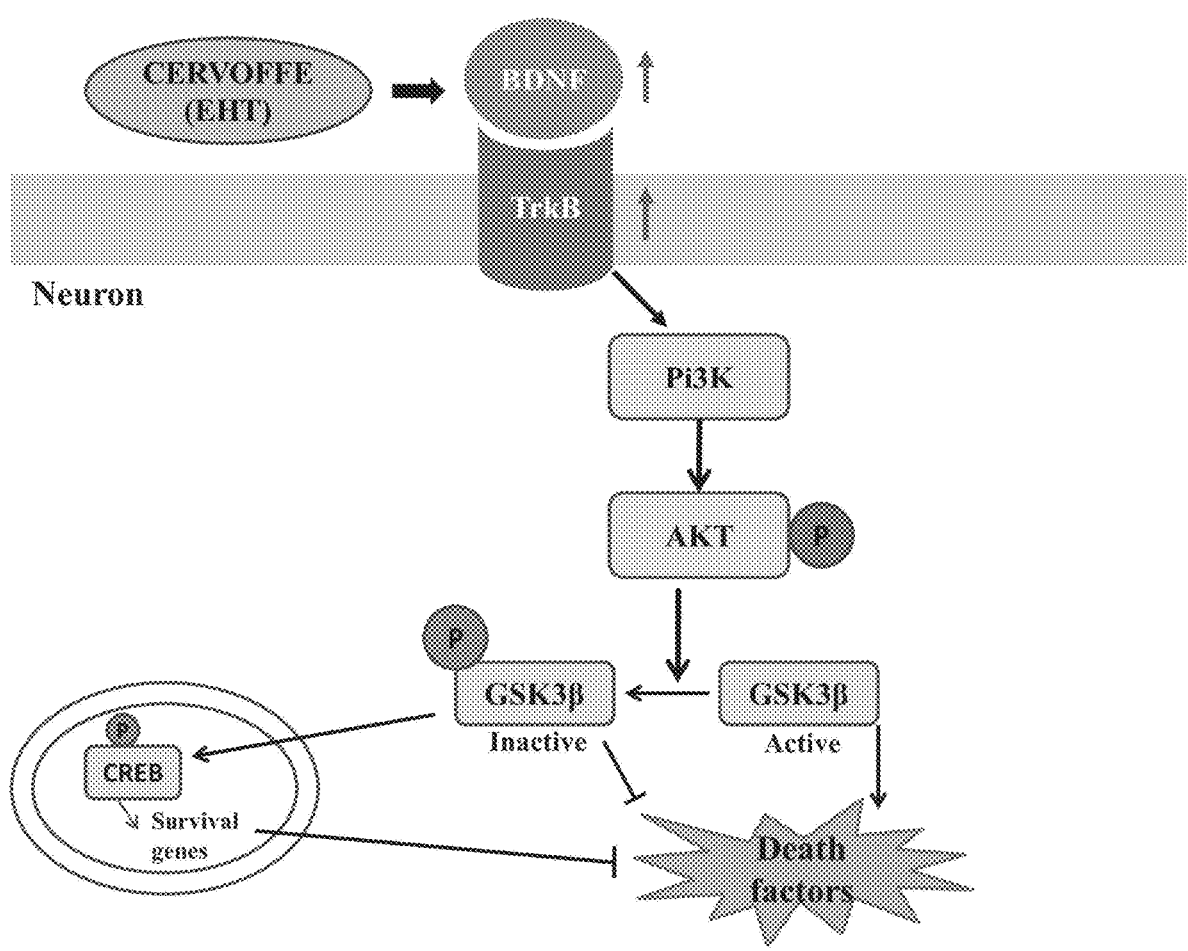
FIG. 8 is a schematic representation of a mechanism of action.

Western blot analysis was performed to investigate the effect of Cervoffe on BDNF-TrkB signalling in the brain of amnesia mice (FIG. 7). BDNF is a member of the neurotrophin gene family and mediates neuroprotective properties via intracellular signalling pathways triggered by activating TrkB. Interestingly, in this study it was found that pretreatment of mice with 200 and 400 mg/kg Cervoffe upregulated the expression of BDNF in the brain and significantly rescued scopolamine-induced downregulation of BDNF. Expression of TrkB was also markedly increased in the treatment groups compared to scopolamine-induced mice. These data indicate that neuroprotective effect of Cervoffe is mediated by BDNF-TrkB pathway (FIG. 8).

Conclusion

The beneficial effect of Cervoffe was demonstrated in scopolamine-induced amnesia mice. Prophylactic treatment with Cervoffe significantly ameliorated the Alzheimer's disease-like dementia in mice by inhibiting the AchE activity and oxidative stress, and upregulating the BDNF expression in the brain. The findings of this study support a mechanism of action wherein Cervoffe mediated neuroprotection via activation of central cholinergic function which in turn enhances the hippocampal neurogenesis through the cAMP response element-binding protein/brain-derived neurotrophic factor (CREB/BDNF) pathway.

Example 5: Molecular Docking

Methods

Figure 9:
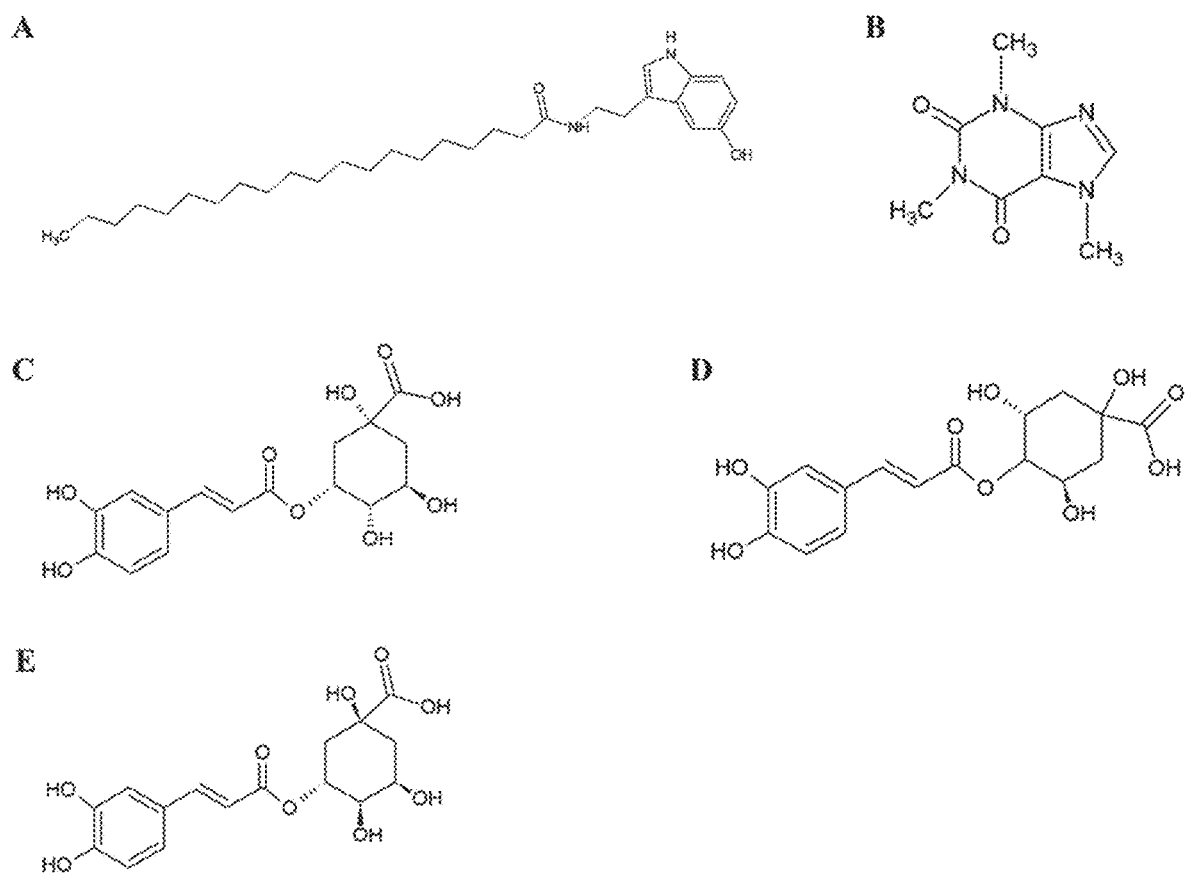
FIG. 9 shows the chemical structure of molecules used for docking analysis. (A) Eicosanoyl-5-hydroxytryptamide (EHT), (B) caffeine, (C) 5-O-caffeoylquinic acid (5-CQA), (D) 4-O-caffeoylquinic acid (4-CQA), and (E) 3-O-caffeoylquinic acid (3-CQA)

Cervoffe contains EHT, caffeine, and a combination of chlorogenic acids. The chemical structures of compounds used for molecular docking are presented in FIG. 9.

The protein druggability assessment was made using PockDrug-Server (Borrel et al. 2015). The molecular docking study was performed using Autodock 4.2 software. AutoDock tools were utilized to generate grids, calculate dock scores, and evaluate the conformers of EHT, caffeine and chlorogenic acids bound in the kinase domain of Plk-2 protein. Docking analysis and binding scores were determined by the Lamarckian genetic algorithm method. The ligand molecules were designed, and the structure was analyzed using ACD/Chemsketch. The PRODRG server was used to minimize energy of drug compounds and 3D coordinates were prepared. The protein structure file (PDB ID: 4i6b) was taken from PDB and edited by removing the hetero atoms using Python molecule viewer. The grid map was centred at particular residues of the protein and was generated with AutoGrid. As per genetic algorithm, all the torsions were allowed to rotate during docking. The Lamarckian genetic algorithm and the pseudo-Solis and Wets methods were applied for minimization, using default parameters (Rodriguez and Infante, 2011).

Results and Discussion

Druggability is a prerequisite for a successful drug discovery. Detecting a targeted protein's ability to bind molecules with high affinity is a key step in identifying molecular targets for therapeutic intervention. In the present study, the pocket prediction of Plk-2 for druggability was determined using PockDrug-Server. As shown in Table 3, Plk-2 was predicted to have average druggability probability of 0.9±0.01. Based on these results, the selected pocket was identified as druggable.

TABLE 4

Pocket Druggability of the Target proteins Lk

| Pockets | Vol. Hull* | Hydroph. Kyte* | Polar Res.* | Aromatic Res.* | Otyr atom | Nb. Res.* | Drugg Prob* | Standard Deviation |
|---|---|---|---|---|---|---|---|---|
| Plk-2 | 20722.35 | −0.59 | 0.61 | 0.18 | 0.0 | 51.0 | 0.9 | 0.01 |

Vol Hull* = Volume Hull;
Hydrophob. Kyte* = Hydrophobic Kyte;
Polar Res.* = Polar Residues Proportion;
Aromatic Res.* = Aromatic Residues Proportion (F, Y, H, W);
Drugg Prob* = Druggability Probability;
Nb. Res.* = Number of pocket residues Molecular Docking—Interaction of Composition with Kinase Domain of Plk-2

Polo-like kinase 2 (Plk-2) is a key protein involved in the Parkinson's Disease pathogenesis (Inglis et al. 2009). Parkinson's Disease pathogenesis is characterized by the accumulation of α-synuclein phosphorylated at Ser-129 (Kruger et al. 1998). Plk-2 is a major contributor to the α-synuclein phosphorylation in the central nervous system (Waxman and Giasson, 2008). Owing to the importance of Plk-2 in Parkinson's Disease pathology, several inhibitors have been previously evaluated for selective inhibition of the protein (Aubele et al. 2013).

Figure 10:
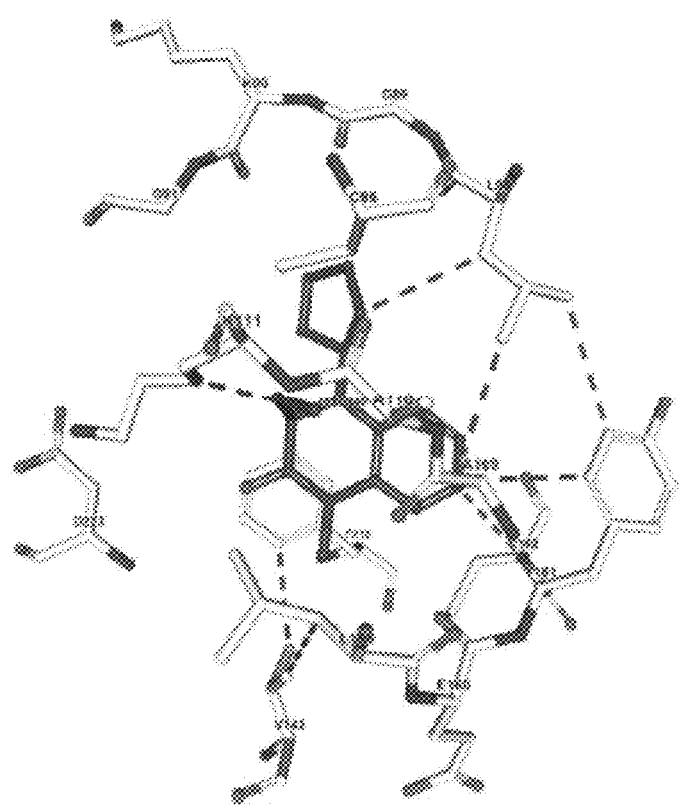
FIG. 10 is a ligand interaction diagram showing the key amino acids in the active site of Plk-2 kinase domain.
Figure 11:
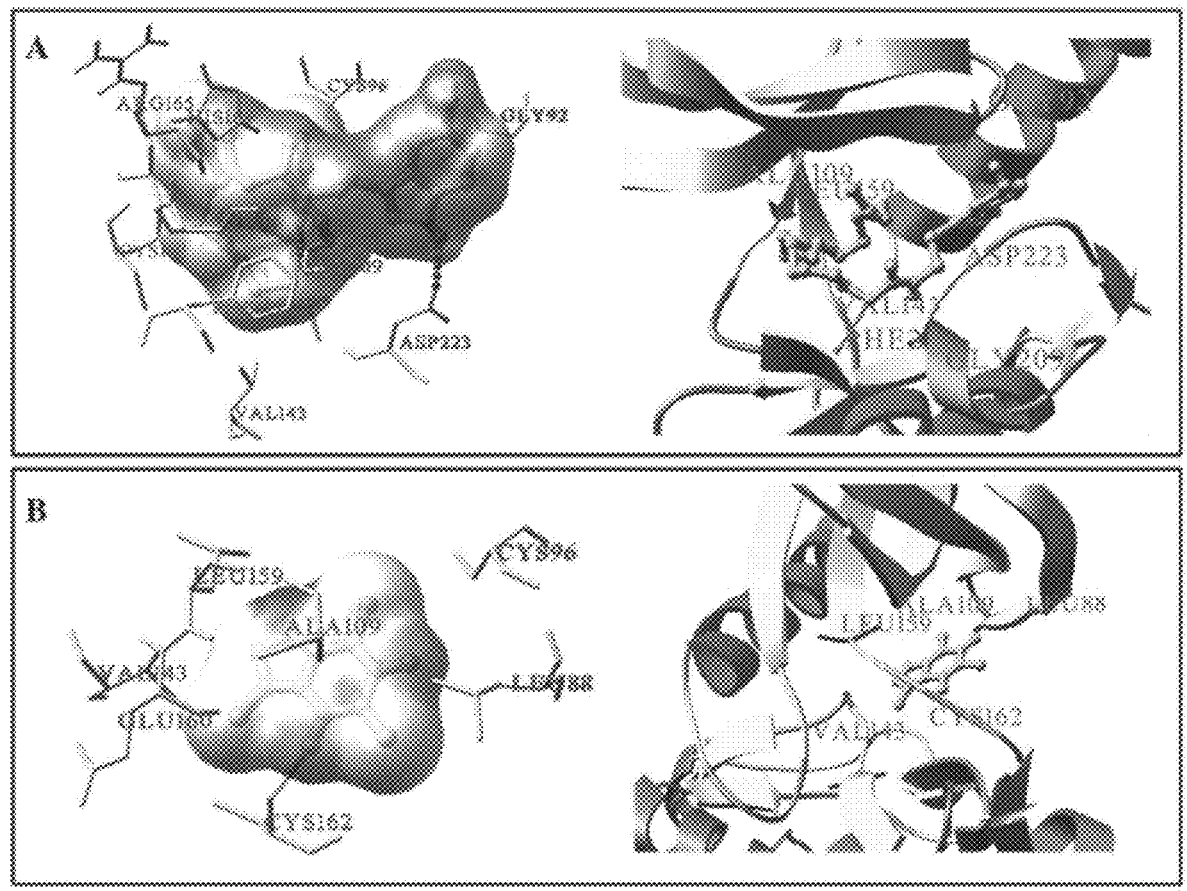
FIG. 11 shows in silico docking analysis of active constituents from an embodiment of the inventive composition with kinase domain of Plk-2. Representative images show interaction of (A) EHT and (B) caffeine with active site amino acids.

Structurally, Plk-2 contains two domains: the kinase domain and the polo box domain. The kinase domain is responsible for the phosphorylation of α-synuclein. FIG. 10 shows the key amino acid residues in the active site of the Plk-2 kinase domain, interacting with a selective Plk-2 inhibitor (www.rcsb.org). We have performed the in silico analysis to predict the interaction of the major bioactive principles of Cervoffe (EHT and caffeine), and chlorogenic acids with the pocket residues in the kinase domain of Plk-2. In our study, the bioactive molecules in Cervoffe showed profound interaction with the active site of Plk-2 (Table 4). The top binding conformations of EHT and caffeine were predicted to have binding energies of −5.63 and −5.64 kcal/mol respectively. EHT had strong H-bonding with amino acid residues Asp223 and Gly209, while caffeine interacted with Cys162 through H-bonding. In addition, both EHT and caffeine showed hydrophobic interactions with Ala109, Val143, Leu159 (FIGS. 11A and 11B). The Ki value recorded for the EHT was 74.56 μM.

Figure 12:
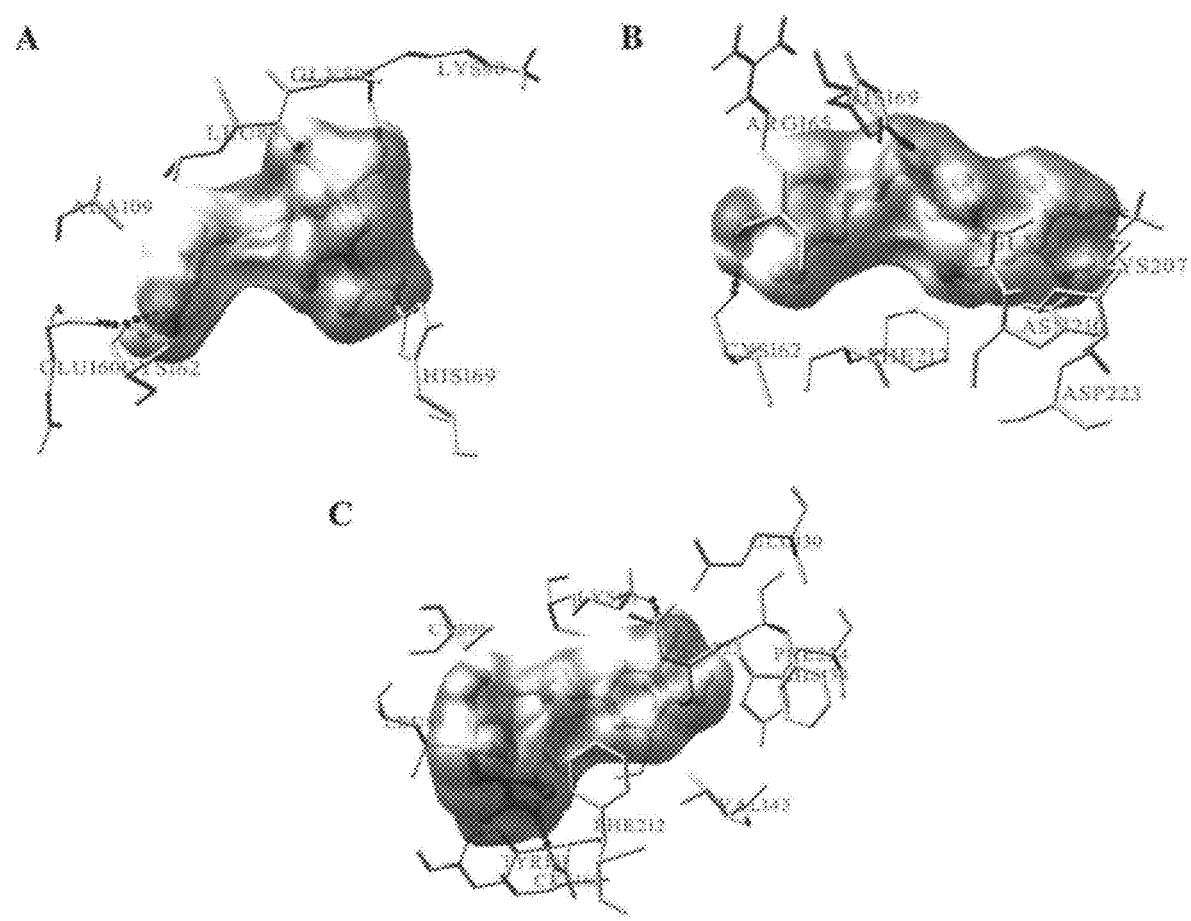
FIG. 12 is a diagrammatic representation of protein ligand interactions between chlorogenic acids and kinase domain of Plk-2. (A) 5-CQA, (B) 4-CQA, and (C) 3-CQA bound conformations into active site in kinase domain of Plk-2.

The chlorogenic acids also exhibited moderate interactions with the key amino acid residues in the active pocket (Table 4, FIG. 12). Among the chlorogenic acid isomers, 3-CQA and 5-CQA showed more favorable interaction with the protein active site, with binding energies of −7.23 and −7.06 kcal/mol, and inhibitory constants 5.01 and 6.67 kcal/mol respectively. The chlorogenic acids commonly interacted with Cys162 amino acid through hydrogen bonding. The interaction of chlorogenic acids was further evident from the hydrophobic contacts with the residues in the kinase domain of Plk-2.

These predictions demonstrate a role of the active principles in Cervoffe in inhibiting Plk-2 protein. A combination of Cervoffe and CGA-7 is expected to show a synergistic effect in reducing the accumulation of phosphorylated α-synuclein via inhibition of Plk-2. Plk-2 inhibition could be an effective strategy in ameliorating Parkinson's Disease symptoms and modulating the disease progression by lowering the α-synuclein levels.

TABLE 5

Docking Score of Constituents of the Composition with Kinase domain of Plk-2

| Molecule | Binding energy kcal/mol | Inhibitory constant (μM) | H-bond | Hydrophobic interactions |
|---|---|---|---|---|
| EHT | −5.63 | 74.56 | Asp223, Gly209 | Gly92, Ala109, Val143, Leu159, Phe212 |
| Caffeine | −5.64 | 143.89 | Cys163 | Leu88, Val143, Leu159, Ala109 |
| 5-CQA | −7.06 | 96.67 | Leu88, Lys90, Glu160, Cys162, His169 | Ala109, Gly89 |
| 4-CQA | −5.65 | 112.46 | Cys162, His169, Arg165, Lys207, Asn210 | Phe212, Gly209 |
| 3-CQA | −7.23 | 95.01 | Asp223, Cys162, Lys111 | Phe212, Phe224, Val143, |

CONCLUSION

The binding interactions of Cervoffe with a target of Parkinson's disease therapy were investigated. Results from the in silico analysis provide the first evidence on the ability of EHT and caffeine in Cervoffe to inhibit Plk-2 protein thus reducing the accumulation of α-synuclein which is the major characteristic of Parkinson's disease pathology. Further, in the combination of Cervoffe with the selected chlorogenic acids, the chlorogenic acids can have appreciable interactions with the Plk-2 kinase domain. This data indicates Cervoffe, with and without the selected chlorogenic acids, can have a neuroprotective effect against Parkinson's disease pathology.

The foregoing description, examples, and accompanying drawings to which the refer are intended to describe some, but not necessarily all, embodiments of the invention. The described embodiments are to be considered in all respects only as illustrative and not restrictive. The contents of this detailed description and the accompanying drawings do not limit the scope of the invention in any way.

REFERENCES

1. Uddin M S, Nasrullah M, Hossain M S, Rahman M M, Sarwar M S, Amran M S, et al. Evaluation of nootropic activity of *Persicaria flaccida* on cognitive performance, brain antioxidant markers and acetylcholinesterase activity in rats: implication for the management of Alzheimer's disease. Am J Psychiatry Neurosci 2016; 426-37.
2. Dhingra D, Kumar V. Memory-enhancing activity of palmatine in mice using elevated plus maze and morris water maze. Adv Pharmacol Sci 2012; 2012: 357368.

3. Agrawal R, Tyagi E, Saxena G, Nath C. Cholinergic influence on memory stages: A study on scopolamine amnesic mice. Indian J Pharmacol 2009; 41(4):192-6.
4. Kwon S H, Lee H K, Kim J A, Hong S I, Kim H C, Jo T H, et al. Neuroprotective effects of chlorogenic acid on scopolamine-induced amnesia via anti-acetylcholinesterase and anti-oxidative activities in mice. Eur J Pharmacol 2010; 649 (1-3): 210-7.
5. Ghumatkar P J, Patil S P, Jain P D, Tambe R M, Sathaye S. Nootropic, neuroprotective and neurotrophic effects of phloretin in scopolamine induced amnesia in mice. Pharmacol Biochem Behav 2015; 135:182-91.
6. Tanzi R E, Bertram L. Twenty years of the Alzheimer's disease amyloid hypothesis: a genetic perspective. Cell 2005; 120: 545-555.
7. Ali T, Yoon G H, Shah S A, Lee H Y, Kim M O. Osmotin attenuates amyloid beta-induced memory impairment, tau phosphorylation and neurodegeneration in the mouse hippocampus. Sci Rep 2015; 5:11708.
8. Alzheimer's Association (2017). 2017 Alzheimer's disease facts and figures. Alzheimers Dement 13: 325-373.
9. Lee J S, Kim H G, Lee H W, Han J M, Lee S K, Kim D W, et al. Hippocampal memory enhancing activity of pine needle extract against scopolamine-induced amnesia in a mouse model. Sci Rep 2015; 14(5): 9651.
10. Ding Q, Dimayuga E, Keller J N. Oxidative damage, protein synthesis, and protein degradation in Alzheimer's disease. Curr Alzheimer Res 2007; 4(1): 73-9.
11. Dugger B N, Dickson D W. Pathology of neurodegenerative diseases. Cold Spring Harb Perspect Biol 2017; 9(7): pii: a028035
12. Meca R, Balbo B E, Ormanji M S, Fonseca J M, Iannuzzi L R, Santana Costa E, et al. Caffeine accelerates cystic kidney disease in a Pkdl-deficient mouse model. Cell Physiol Biochem 2019; 52(5): 1061-1074.
13. Aubele D L, Hom R K, Adler M, Galemmo R A Jr, Bowers S, Truong A P, et al. Selective and
14. brain-permeable polo-like kinase-2 (Plk-2) inhibitors that reduce α-synuclein phosphorylation in rat brain. Chem Med Chem 2013; 8(8): 1295-313.
15. Boll M C, Alcaraz-Zubeldia M, Rios C. Medical management of parkinson's disease: focus on neuroprotection. Curr Neuropharmacol 2011; 9(2): 350-359.
16. Borrel A, Regad L, Xhaard H G, Petitjean M, Camproux A C. PockDrug: a model for predicting pocket druggability that overcomes pocket estimation uncertainties. J Chem Inf Model 2015
17. Colovic M B, Krstic D Z, Lazarevic-Pasti T D, Bondzic A M, Vasic V M. Acetylcholinesterase inhibitors: pharmacology and toxicology. Current Neuropharmacol 2013; 11(3): 315-335.
18. Colovic M B, Krstic D Z, Lazarevie-Pagti T D, Bondzie A M, Vasic V M. Acetylcholinesterase inhibitors: pharmacology and toxicology. Curr Neuropharmacol 2013; 11(3): 315-335.
19. Hameleers P. Habitual caffeine consumption and its relation to memory, attention, planning capacity and psychomotor performance across multiple age groups. Hum Pychopharmacol Clin Exp 2000; 15: 573-81.
20. Inglis K J, Chereau D, Brigham E F, Chiou S S, Schobel S, Frigon N L, et al. Polo-like kinase 2
21. (PLK2) phosphorylates alpha-synuclein at serine 129 in central nervous system. J Biol Chem 2009; 284(5): 2598-2602.
22. Kruger R, Kuhn W, Muller T, Woitalla D, Graeber M, Kosel S, et al. Nat. Genetics 1998; 18: 106-108.
23. Olin J, Schneider L. Galantamine for Alzheimer's disease. Cochrane Database of Systematic Reviews 2002; 3CD001747
24. Parvez M K. Natural or plant products for the treatment of neurological disorders: current knowledge. Curr Drug Metab 2018; 19(5): 424-428.
25. Rodriguez A, Infante D. Characterization in silico of flavonoids biosynthesis in *Theobroma cacao* L. Net Biol 2011; 1: 34-45.
26. Waxman E A, Giasson B I. Specificity and regulation of casein kinase-mediated phosphorylation of alpha-synuclein. J Neuropathol Exp Neurol 2008; 67: 402-416.
27. Yan R, Zhang J, Park H J, Park E S, Oh S, Zheng H, et al. Synergistic neuroprotection by coffee components eicosanoyl-5-hydroxytryptamide and caffeine in models of Parkinson's disease and DLB. 2018; 115(51): E12053-E12062.

The invention claimed is:

1. A method of treating a neurodegenerative disorder, comprising administering to a patient in need thereof an effective amount of a composition comprising about 10% w/w eicosanoyl-5-hydroxytryptamide, wherein administering said composition treats said neurodegenerative disorder and wherein said composition further comprises about 0.40% w/w octadecanoic hydroxytryptamide, about 0.30% w/w heneicosanoic hydroxytryptamide, about 4.60% w/w docosanoic hydroxytryptamide, about 0.40% w/w tricosanoic hydroxytryptamide, about 0.90% w/w tetracosanoic hydroxytryptamide, and about 0.10% pentacosanoic hydroxytryptamide.

2. The method of claim 1, wherein said composition comprises 0.42% w/w octadecanoic hydroxytryptamide, 0.27% w/w heneicosanoic hydroxytryptamide, 4.55% w/w docosanoic hydroxytryptamide, 0.39% w/w tricosanoic hydroxytryptamide, 0.85% w/w tetracosanoic hydroxytryptamide, and 0.06% pentacosanoic hydroxytryptamide, and said eicosanoic hydroxytryptamide is present in an amount of 10.17% w/w.

3. The method of claim 1, wherein said composition further comprises caffeine.

4. The method of claim 1, wherein said composition further comprises a mixture of chlorogenic acids that includes 3-CQA, 5-CQA, 4-CQA, 5-FQA, 3,4-diCQA, 3,5-diCQA, and 4,5-diCQA.

5. The method of claim 1, wherein said neurodegenerative disorder is Alzheimer's disease or Parkinson's disease.

6. The method of claim 1, wherein said patient is at risk of developing said neurodegenerative disorder, and administering said composition inhibits at least one of the development of said neurodegenerative disorder and the symptoms of said neurodegenerative disorder.

7. The method of claim 1, wherein said patient is at risk of developing Alzheimer's disease and administering said composition inhibits at least one of cognitive decline and memory impairment.

8. The method of claim 1, wherein said patient is a human.

9. The method of claim 1, wherein said composition is administered at a dose of between about 200 mg/kg and about 400 mg/kg.

10. The method of claim 1, wherein said composition is an administration form selected from: a powder; liquid; pill; tablet; pellet; capsule; thin film; solution; spray; syrup; linctus; lozenge; pastille; chewing gum; paste; vapor; suspension; emulsion; ointment; cream; lotion; liniment; gel;

drop; topical patch; buccal patch; bead; gummy; sol; injection; and combinations thereof.

11. The method of claim 1, wherein said composition further comprises at least one of a vitamin, mineral, extract, amino acid, protein, carbohydrate, lipid, fatty acid, food, beverage, nutritional supplement, dietary supplement, excipient, pharmaceutically acceptable carrier, bulking agent, binding agent, caffeine, flavoring, sweetener, and preservative.

12. The method of claim 1, wherein said composition is administered systemically.

13. The method of claim 1, wherein said composition is administered by a route selected from the group consisting of: orally; buccally; sub-lingually; topically; parenterally; intravenously; intravaginally; rectally; by inhalation; and combinations thereof.

14. The method of claim 1, wherein said composition is administered orally.

15. The method of claim 1, wherein said composition is a coffee bean extract.

16. A composition for treating a neurodegenerative disorder, comprising about 10% w/w eicosanoyl-5-hydroxytryptamide wherein said composition further comprises about 0.40% w/w octadecanoic hydroxytryptamide, about 0.30% w/w heneicosanoic hydroxytryptamide, about 4.60% w/w docosanoic hydroxytryptamide, about 0.40% w/w tricosanoic hydroxytryptamide, about 0.90% w/w tetracosanoic hydroxytryptamide, and about 0.10% pentacosanoic hydroxytryptamide.

17. The composition of claim 16, wherein said composition comprises 0.42% w/w octadecanoic hydroxytryptamide, 0.27% w/w heneicosanoic hydroxytryptamide, 4.55% w/w docosanoic hydroxytryptamide, 0.39% w/w tricosanoic hydroxytryptamide, 0.85% w/w tetracosanoic hydroxytryptamide, and 0.06% pentacosanoic hydroxytryptamide, wherein said eicosanoic hydroxytryptamide is present in an amount of 10.17% w/w.

18. The composition of claim 16, wherein said composition further comprises caffeine.

19. The composition of claim 16, wherein said composition further comprises a mixture of chlorogenic acids that includes 3-CQA, 5-CQA, 4-CQA, 5-FQA, 3,4-diCQA, 3,5-diCQA, and 4,5-diCQA.

20. The composition of claim 16, wherein said composition is an administration form selected from: a powder; liquid; pill; tablet; pellet; capsule; thin film; solution; spray; syrup; linctus; lozenge; pastille; chewing gum; paste; vapor; suspension; emulsion; ointment; cream; lotion; liniment; gel; drop; topical patch; buccal patch; bead; gummy; gel; injection; and combinations thereof.

21. The composition of claim 16, wherein said composition further comprises at least one of a vitamin, mineral, extract, amino acid, protein, carbohydrate, lipid, fatty acid, food, beverage, nutritional supplement, dietary supplement, excipient, pharmaceutically acceptable carrier, bulking agent, binding agent, caffeine, flavoring, sweetener, and preservative.

22. The composition of claim 16, wherein said composition further comprises an artificial excipient.

* * * * *